(12) United States Patent
Yurkovsky et al.

(10) Patent No.: US 10,941,061 B1
(45) Date of Patent: Mar. 9, 2021

(54) THERAPEUTIC FREQUENCY IMPRINTING DEVICE

(71) Applicants: Savely Yurkovsky, Ridgefield, CT (US); Cyril William Smith, Manchester (GB)

(72) Inventors: Savely Yurkovsky, Ridgefield, CT (US); Cyril William Smith, Manchester (GB)

(*) Notice: Subject to any disclaimer, the term of this patent is extended or adjusted under 35 U.S.C. 154(b) by 60 days.

(21) Appl. No.: 16/544,674

(22) Filed: Aug. 19, 2019

(51) Int. Cl.
  *C02F 1/48* (2006.01)
  *A61K 41/00* (2020.01)

(52) U.S. Cl.
  CPC ............ *C02F 1/48* (2013.01); *A61K 41/0004* (2013.01); *C02F 2201/483* (2013.01)

(58) Field of Classification Search
  CPC ... C02F 1/48; C02F 2201/483; A61K 41/0004
  See application file for complete search history.

(56) References Cited

U.S. PATENT DOCUMENTS

2017/0072210 A1* 3/2017 Gangwish ................ A61N 2/02

FOREIGN PATENT DOCUMENTS

CN         1987203500 U  *  5/1988

* cited by examiner

*Primary Examiner* — Waqaas Ali

(57) ABSTRACT

A therapeutic frequency imprinting device is used to determine a therapeutic frequency from a biological specimen known to cause an ailment in a patient, and subsequently imprint the therapeutic frequency into a carrier agent for treatment of the ailment. The specimen is placed into an in-well, which is electrically connected to a potentiometer. The resistance of the potentiometer is adjusted in order to modulate the magnetic vector potential component of the magnetic field radiated by a conductive coil connected between the potentiometer and an out-well in which a carrier substance is placed to be imprinted with the therapeutic frequency.

5 Claims, 5 Drawing Sheets

THERAPEUTIC FREQUENCY IMPRINTING DEVICE

FIELD OF THE INVENTION

The present invention relates generally to therapy for treating ailments. More particularly, the present invention relates to a device for using bio-information to imprint a therapeutic frequency onto a carrier medium for treatment.

BACKGROUND OF THE INVENTION

From a background of 40 years research into the interactions of electromagnetic fields and frequencies with bio-systems the Sine Qua Non is that a coherent frequency can have a biological effect. Work up to 2006 is summarized in a chapter in the Fröhlich-Festschrift and subsequently in the 2015 update chapter in 'Ultra-high Dilution.'

Frequency is the number of times per second that the pattern of something in oscillation repeats itself. A number of oscillators are coherent if their waveforms can be superimposed and the degree of coherence is determined by statistical fluctuations in the number oscillators involved in the coherence.

A frequency can be the frequency of a "Classical Electromagnetic Field" which is the basis of electronics and radio, it describes oscillations whose phase is well defined but for which the number of particles carrying the energy is undefined. Frequency can be the frequency of a "Quantum Field" which takes account of waves behaving like particles (photons). Here, there is uncertainty in both the phase of the wave property and in the number of particles involved in the coherence. The more the uncertainty is taken up by fluctuation in the number of particles, the more perfect is the coherence. This uncertainty is quantified by the Heisenberg Uncertainty Relation.

Bio-information is carried on the magnetic vector potential component (A-field) of the magnetic field. The magnetic B-field component is equivalent to a momentum impulse (succession) and has a frequency imprinting function. The A-field is a mathematical consequence of the B-field occurring in closed loops.

A frequency modulated on an oscillating A-field is imprinted ("remembered") into water or other medium through spin precession of protons and electrons in the geomagnetic field. If imprinted water is placed in a steel box so as to reduce the ambient magnetic field below a certain critical value, any imprint is erased by thermal agitation.

Any chemicals (including allopathics) which can interact with trace water develop characteristic frequency signatures which can also have a biological effect. Two chemicals used in this work with unusual frequency signatures are hydrogen peroxide ($H_2O_2$) and formaldehyde (HOCO). These chemicals give a continuum of frequency rather than discrete frequency values. Hydrogen peroxide (6%) has an L-chirality (stimulatory) continuum from 2 µHz to 6.5 GHz. Formaldehyde (1%) has a D-chirality (depressive) continuum from 4 µHz to 6 GHz and is a good trigger for electromagnetic hypersensitivities.

In a coherent system, the distance over which the coherence persists (coherence length) replaces velocity (e.g. that of light) as the constant parameter. This gives the possibility of many frequencies each proportional to a velocity the system will support. The result is a 'multiple frequency' (fractal-like) effect enabling chemical, technological and biological frequency bands to interact over a wide frequency range extending from the optical to the circadian. Coherence propagates by diffusion, in air coherent frequencies propagate by diffusion through ambient atmospheric water vapor and on surfaces along a film of moisture.

In 1982, a task was undertaken to help with the problems experienced by chemically sensitive patients who had become hypersensitive to their electromagnetic environment. The symptoms provoked in them by the chemicals to which they had acquired a hypersensitivity were identical to those triggered by specific frequencies in their environment. It quickly became clear that it was frequency that mattered and that each frequency was patient specific. For a chemically sensitive patient with seven allergic chemicals, some frequency sensitivity would be expected to be found. With nine allergic chemicals, it would be surprising not to. This led to the development of techniques for the measurement of frequencies, first in patients, then in water.

The provocation/neutralization technique used for treating allergy patients involves making a set of serial dilutions of allergens and testing them on the patient to see which dilution stops the allergic reaction. This then is used for therapy. Tuning oscillators through a wide range of frequencies in front of patients gave similar provocation/neutralization reactions at specific frequencies. Patients' allergies could be neutralized either by a serial dilution of the allergen, by the frequency from the oscillator or by the frequency imprinted into water.

The whole of the electromagnetic spectrum is used by living systems. Acupuncture Meridians carry endogenous frequencies ranging from 500 µHz to 300 GHz and Chakra Points from 0.25 Hz to 3.9 GHz. These frequencies are usually confined to the meridians or points. But, the appearance of one of these frequencies in the whole-body field indicates stress on the related target organ. This can be used for diagnostic purposes.

It is therefore an objective of the present invention to present an apparatus through which a therapeutic frequency may be determined from a biological, pathogenic, or morbid specimen, toxicological agent, or other specimens, agents or materials known to cause an ailment in a patient, and subsequently imprint the therapeutic frequency into a carrier agent such as water for treatment of the ailment.

Additional advantages of the invention will be set forth in part in the description which follows, and in part will be obvious from the description, or may be learned by practice of the invention. Additional advantages of the invention may be realized and attained by means of the instrumentalities and combinations particularly pointed out in the detailed description of the invention section. Further benefits and advantages of the embodiments of the invention will become apparent from consideration of the following detailed description given with reference to the accompanying drawings, which specify and show preferred embodiments of the present invention

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

This present invention is an apparatus for addressing the problem of getting the body to produce a beneficial biological reaction against a morbid agent using the coherent frequency information field of that same morbid agent for therapy or prophylaxis. A patient is challenged with coherent frequency information and through established techniques such as heart-rate-variability, electro-acupuncture, and/or kinesiology, the patient's response is assessed. Then a therapeutic frequency setting is selected and imprinted into water or other carrier suitable for therapy.

Figure 1:
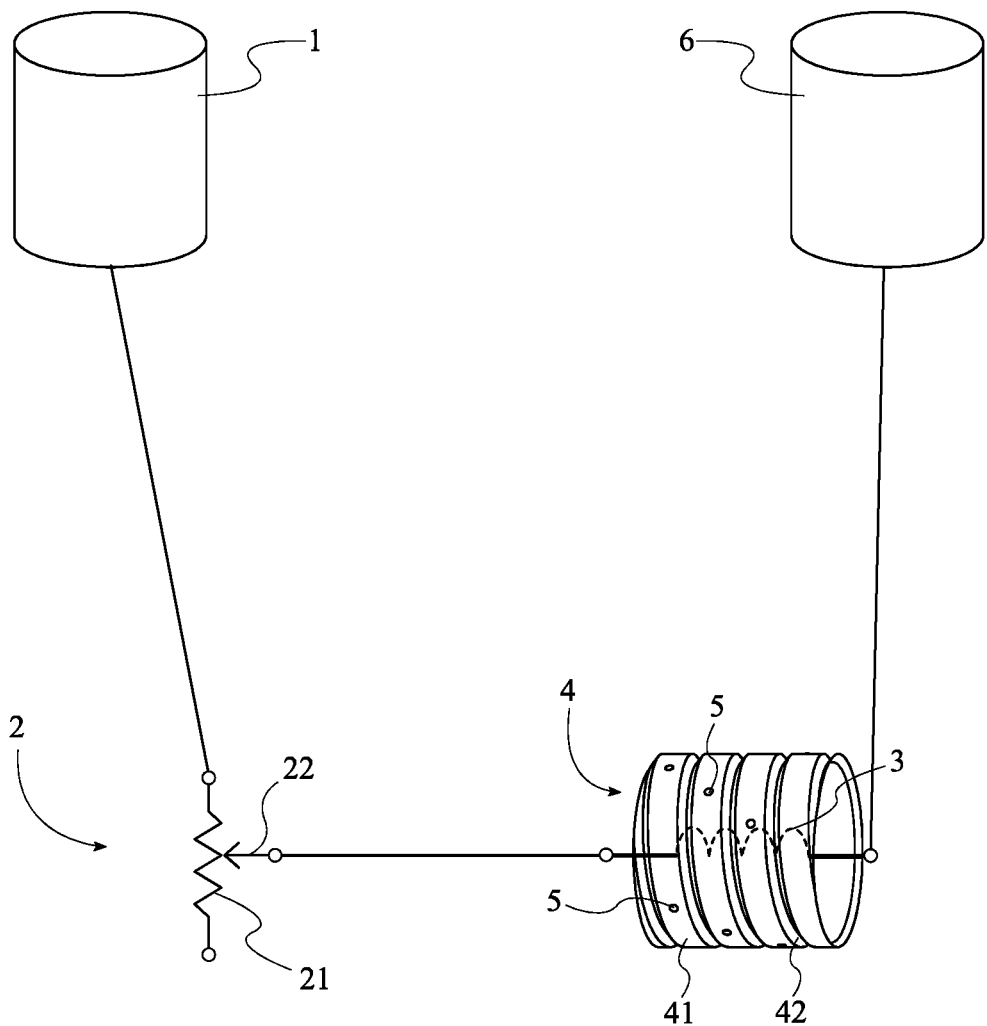
FIG. 1 is a diagram illustrating the main apparatus of the present invention.
Figure 3:
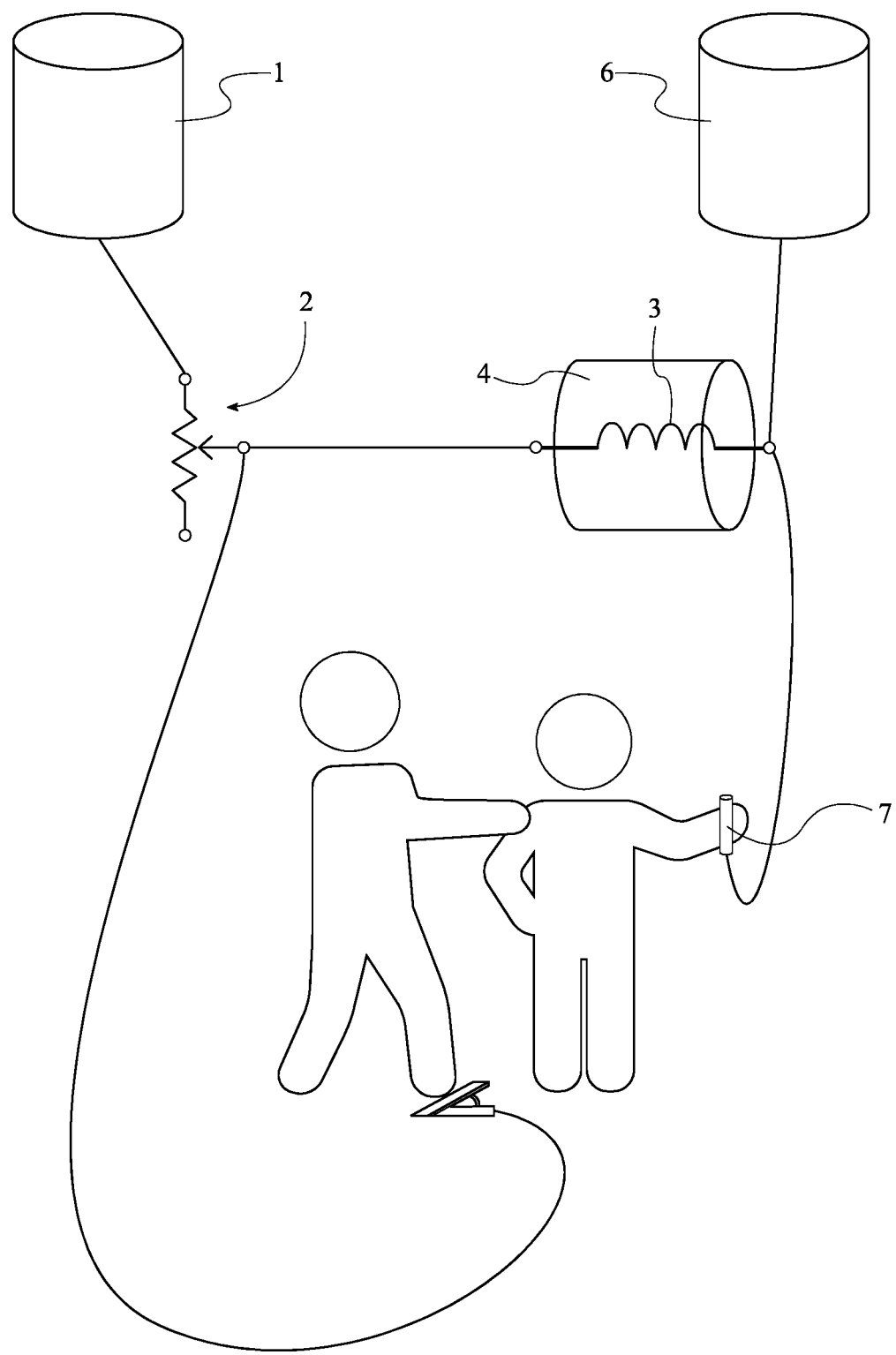
FIG. 3 is a diagram illustrating the present invention in use to determine an optimal frequency for treatment of a patient.

In general, referring to FIG. 1, the present invention comprises an in-well 1, a potentiometer 2, a conductive coil 3, a shielding tube 4, a plurality of magnets 5, and an out-well 6. The in-well 1 is electrically connected to the potentiometer 2, and the potentiometer 2 is electrically connected between the in-well 1 and the conductive coil 3. The conductive coil 3 is positioned within the shielding tube 4, and the plurality of magnets 5 is connected to the shielding tube 4. Finally, the conductive coil 3 is electrically connected between the potentiometer 2 and the out-well 6. Furthermore, in some embodiments, a conductive probe 7 may be included, as shown in FIG. 3. The conductive probe 7 may be electrically connected to the conductive coil 3 and is used to assess patient response. The conductive probe 7 may be a handlebar, a wristband, a headband, or simply a conductive wire, or any other relevant apparatus.

It should be noted herein that the relation "electrically connected" simply means that there is at least one electrically conductive path between the components being related. The electrical connection may be accomplished with one or more conductive wires, or through direct contact between conductive elements, or through any other desirable means. The use of "electrically connected" is not intended to necessarily imply the flow of an electric current along the connection between electrically connected components, only the presence of an electrically conductive connection. In some embodiments, the present invention does not require a designated source of electrical power, as frequencies are understood to pass along the various electrical connections by diffusion.

In the preferred embodiment of the present invention, the in-well 1 and the out-well 6 are each a hollow copper container. Donor material, such as a biological or chemical specimen known to cause an adverse reaction in a patient, is placed into the in-well 1. The in-well 1 is electrically connected to the potentiometer 2 through a single lead. The coherent frequencies pass along the wire by diffusion. Similarly, the out-well 6 is a hollow container also made of copper in the preferred embodiment. The purpose of the out-well 6 is to contain a carrier material or substance, and imprint said substance with a therapeutic frequency originating from the in-well 1 as selected through the setting of the potentiometer 2.

In the preferred embodiment of the present invention, the potentiometer 2 is a standard electronics component having a 10 kΩ linear carbon track of ½ Watt rating in which the resistance between an end terminal of the track and the contacting wiper is determined by the rotational position of a shaft as indicated by a pointer and dial inscribed with graduations marking the position of the wiper. However, the resistance, wattage rating and other attributes of the potentiometer 2 may vary in different embodiments of the present invention.

In the preferred embodiment, the potentiometer 2 comprises a potentiometer track 21 and a contact wiper 22. The in-well 1 is electrically connected to the potentiometer track 21, and the contact wiper 22 is electrically connected between the track and the conductive coil 3, such that the contact wiper 22 is selectably positionable along the potentiometer track 21. The contact wiper 22 may be physically connected to a knob or other device through which the position at which the contact wiper 22 touches the potentiometer track 21 may be selected, either manually by a user, automatically through electrically actuated and computer-controlled mechanisms, or other desired means.

In the preferred embodiment, the shielding tube 4 comprises a body 41 and a threading 42. The threading 42 axially and externally traverses across the body 41. In some embodiments, the threading 42 is oriented clockwise. In some embodiments, the threading 42 is a female threading 42. In the preferred embodiment, the shielding tube 4 is a section of iron pipe that provides an additional shielding of the geomagnetic field and from ambient electromagnetic fields, through the plurality of magnets 5, which are attached to the shielding tube 4. In other embodiments, the shielding tube 4 may comprise alternate configurations or materials that are appropriate to facilitating the aforementioned function of the shielding tube 4.

The A-field modulated with the frequency selected by the potentiometer 2 setting diffuses from the apparatus to a distance of about 4 meters, a typical coherence length in ambient humidity. This is analogous to the propagation of Qi from a healer. It provides space for the tester to use kinesiology or other procedures to assess the patient's condition. Alternatively, the patient may be connected directly to one of the wells using a wire and hand-held electrode, for example. Either would be sufficient to stimulate a patient response to the frequency selected by the potentiometer 2 which has in turn been derived from the material placed in the 'In-well 1' or direct from the patient. The B-field is shielded by the iron shielding tube 4 so there is no risk of a frequency used for challenge becoming imprinted into the patient.

The connection to the out-well 6 carries the selected frequency as both a modulated A-field component and a modulated B-field component which is 180° out of phase with the A-field component. This is a condition for imprinting that frequency into water. Imprinting can be enhanced by placing ferrite magnets at appropriate locations.

The plurality of magnets 5 significantly expedites the speed of transfer of a therapeutic frequency to be imprinted into water or another carrier. The shielding tube 4 has an external clockwise thread cut into its external surface which is equivalent to an external coil of wire and suppresses stressful D-chirality frequencies. The conductive coil 3 is placed inside the shielding tube 4. Preferably, the conductive coil 3 is a coil of copper wire wound in a clockwise sense, whose ends are electrically connected to the potentiometer 2 and the out-well 6 respectively.

Figure 5:
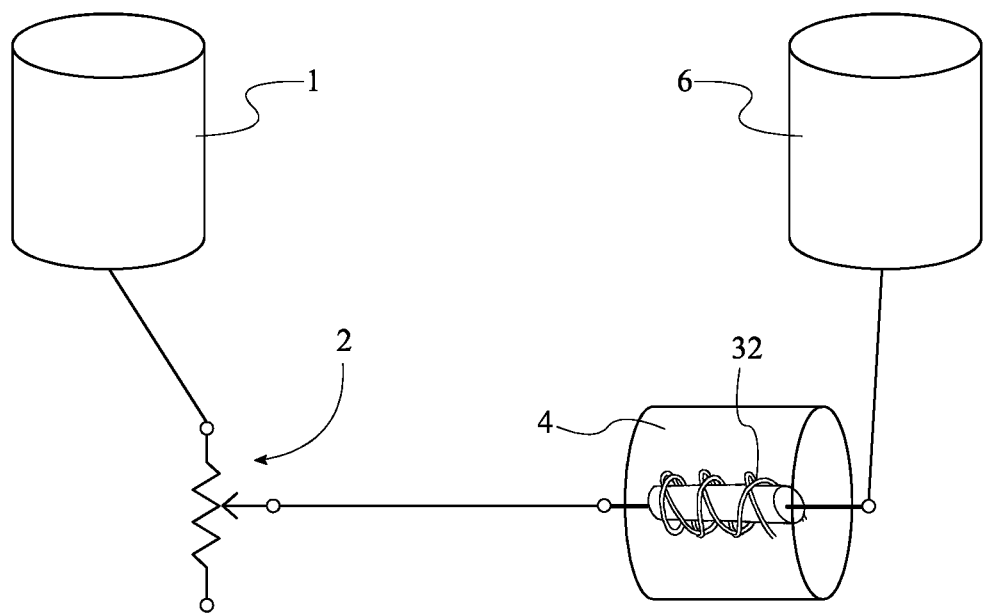
FIG. 5 is a diagram of one embodiment of the present invention comprising a Caduceus or other equivalent coil as the conductive coil.

In various embodiments, the specific nature of the conductive coil 3 may vary. In some embodiments, the conductive coil 3 is a toroid coil 31. In some embodiments, the conductive coil 3 is a Caduceus coil 32, as shown in FIG. 5.

Figure 2:
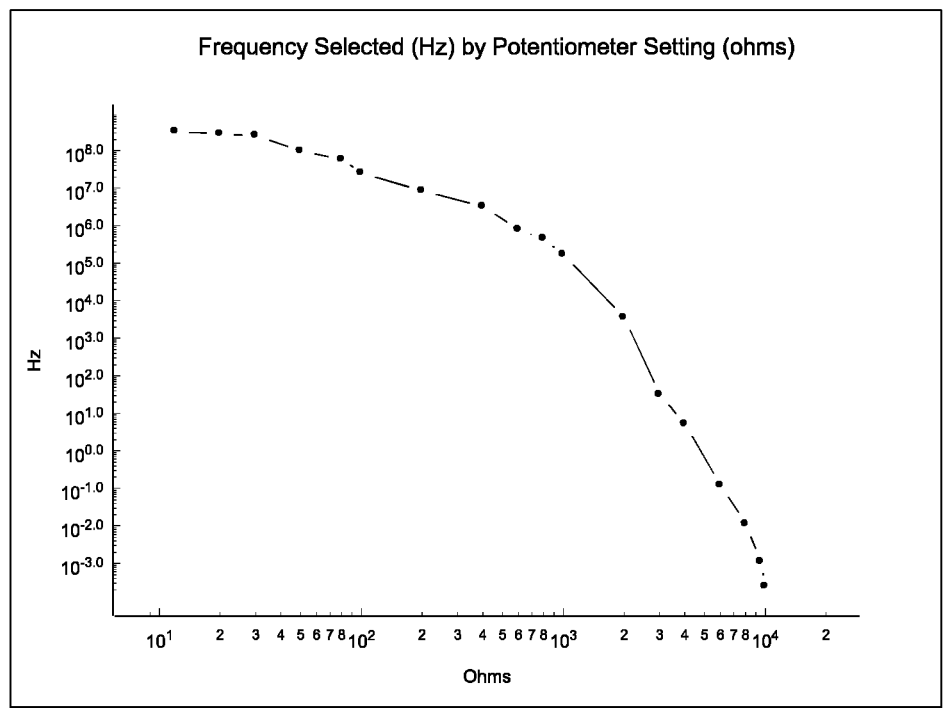
FIG. 2 is an exemplary graph of frequency versus potentiometer resistance using one embodiment of the present invention.

The potentiometer 2 selects a specific frequency from a specimen placed in the in-well 1. In an exemplary instance of use of the present invention, to determine the range of frequencies which could be selected by the potentiometer 2, a bottle of hydrogen peroxide (6%) is placed in the in-well 1. Hydrogen peroxide has an L-chirality (stimulatory) continuum extending from 2 μHz to 65 GHz. The result is shown in FIG. 2. With the potentiometer 2 set at zero resistance, the frequency measured is the water resonance frequency 384 MHz and at the 10 kΩ setting it was 240 μHz. The acupuncture meridians have endogenous frequencies ranging from 500 μHz to 300 GHz. This Apparatus would cover all the lower band meridian frequencies and all the upper band meridian frequencies except the Fibroid Degeneration and Sanjiao (Triple-Warmer) Meridians.

Next, a bottle of formaldehyde (1%) is placed in the in-well 1. No signal was detected, confirming that the apparatus successfully blocked stress frequencies originating from the in-well 1. The physical mechanism by which the apparatus operates involves the properties of trace water. The potentiometer 2 was sealed in a plastic bag containing desiccant silica-gel, the result of which was that all frequency selection and other activity ceased.

Coherence propagation requires the carbon track in the potentiometer to be in ambient humidity and to propagate coherent frequencies with a velocity which is frequency dependent.

The setting of the linear potentiometer (ohms) is equivalent to setting a path length for frequency diffusion.

Velocity=distance÷time=distance×frequency. Thus, the selected frequency varies inversely with distance and thus with ohms.

As shown in FIG. 2 and for that particular potentiometer, the settings provide a measurement range of approximately $10^{11}$ selectable frequencies between or 10Ω and 10 kΩ. Coherent frequencies can be excited by the following coil configurations which generate an A-field without the B-field component. For this reason, the solenoid was not used as its B-field might imprint one of the test frequencies into the patient or water being measured.

Figure 4:
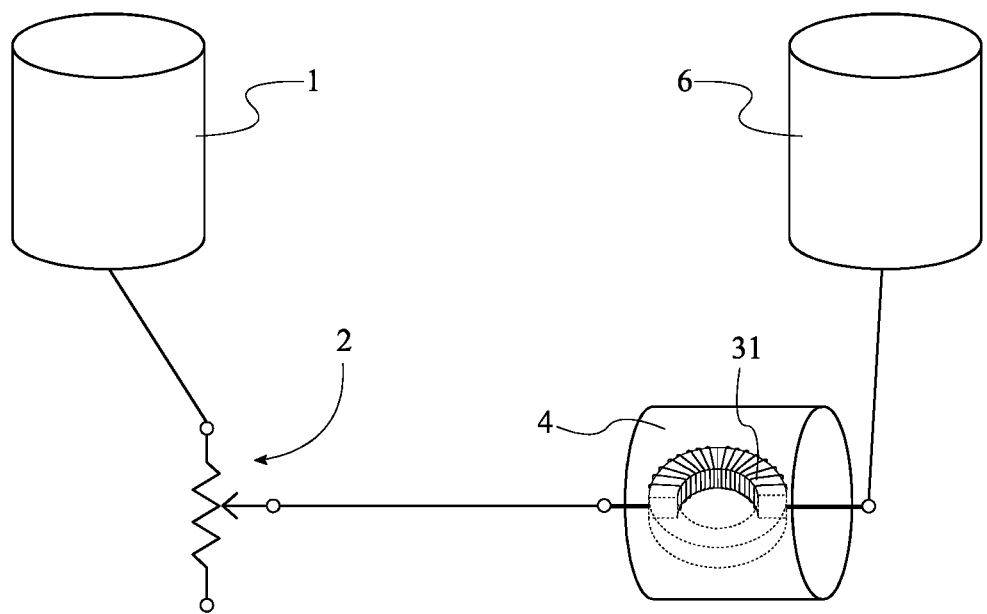
FIG. 4 is a diagram of one embodiment of the present invention comprising a toroid coil as the conductive coil.

As previously mentioned, the conductive coil 3 may vary in different embodiments of the present invention. In some embodiments, the conductive coil 3 may be a toroid coil 31, which is a coil wound around a ring which may be of ferrite, as shown in FIG. 4. The B-field is contained within the ring and the A-field permeates the surrounding space.

In some embodiments, the conductive coil 3 may be a Caduceus coil 32, which is a coil wound like a solenoid for the first layer of wire, but a second layer of wire is then wound back over it in the opposing direction to the first layer of wire. The resulting B-fields cancel so it is often called a 'non-inductive' coil. The tangential components of the A-fields also cancel but, the radial A-field component remains.

FIG. 2 is derived from measurements on a prototype of the present invention. The measurements confirm that the present invention can extract therapeutic bio-information from a specimen placed in the in-well 1 by adjustment of the potentiometer 2. The present invention radiates the frequency bio-information to a distance which is clinically useful for challenging a patient. When the potentiometer 2 has been adjusted to a setting which gives a therapeutically useful result as determined by an appropriate clinical test, that frequency can be imprinted into a medium suitable for therapy or prophylaxis placed in the out-well 6.

In a production instrument, it would be desirable for the operator to be able to control the potentiometer 2 setting from a foot pedal because in a clinical situation the tester usually needs to have both hands free; for example, in the bi-digit ring-test.

In a general method of use of the present invention, a patient is challenged with coherent frequency information. The patient's response is assessed, and a therapeutic frequency is selected using the potentiometer 2. The therapeutic frequency is then imprinted onto water or another suitable carrier medium using the apparatus of the present invention.

In an exemplary treatment scenario, a patient would be tested using a conductive probe 7, embodied as a handlebar or similar device, as shown in FIG. 3. A homeopathically prepared substance, such as, for example, a sample of a pathogen such as Lyme bacteria, is placed into a container such as a glass vial in the in-well 1. A quantity of a carrier substance, such as water, is placed in a container such as a dropper bottle in the out-well 6. A practitioner monitors the patient's muscle response or other stress indicators as the resistance of the potentiometer 2 is changed. The patient senses the radiated frequency field of the specimen in the in-well 1, and the potentiometer 2 setting is modulated in an attempt to determine the optimal setting. The optimal strength of the radiated frequency field is determined by the practitioner judging the patient's muscle response or other kinesiologic stress indicators, such as reflexes. As the frequency field of the specimen is radiated, the patient's body produces stress responses, which are monitored by the practitioner. When the patient starts to release their bodily stress against the specimen's radiated field while sensing the field of the carrier substance in the out-well 6, the practitioner knows that the potentiometer 2 setting is at or near optimal. When the patient is optimally relaxed and their muscle stress or other stress indicators are released, the potentiometer 2 setting is recorded. The apparatus of the present invention is then used to imprint the therapeutic frequency field corresponding to the potentiometer 2 setting. The imprinted carrier substance may then be used to treat the patient.

Although the invention has been explained in relation to its preferred embodiment, it is to be understood that many other possible modifications and variations can be made without departing from the spirit and scope of the invention as hereinafter claimed.

What is claimed is:

1. A therapeutic frequency imprinting device comprises:
an in-well;
a potentiometer;
a conductive coil;
a shielding tube;
a plurality of magnets;
an out-well;
the in-well being electrically connected to the potentiometer;
the potentiometer being electrically connected between the in-well and the conductive coil;

the conductive coil being positioned within the shielding tube;

the plurality of magnets being connected to the shielding tube;

the conductive coil being electrically connected between the potentiometer and the out-well;

the potentiometer comprises a potentiometer track and a contact wiper;

the in-well being electrically connected to the potentiometer track;

the contact wiper being electrically connected between the track and the conductive coil; and the contact wiper being selectably positionable along the potentiometer track.

2. The therapeutic frequency imprinting device as claimed in claim 1 comprises:

a conductive probe; and the conductive probe being electrically connected to the conductive coil.

3. The therapeutic frequency imprinting device as claimed in claim 1 comprises:

the in-well and the out-well each being a hollow copper container.

4. The therapeutic frequency imprinting device as claimed in claim 1 comprises:

the conductive coil being a toroid coil.

5. The therapeutic frequency imprinting device as claimed in claim 1 comprises:

the conductive coil being a caduceus coil.

* * * * *